United States Patent
Campbell

[11] Patent Number: 5,924,997
[45] Date of Patent: Jul. 20, 1999

[54] CATHETER AND METHOD FOR THE THERMAL MAPPING OF HOT SPOTS IN VASCULAR LESIONS OF THE HUMAN BODY

[76] Inventor: Thomas Henderson Campbell, 254 Jeter St., Redwood City, Calif. 94062

[21] Appl. No.: 08/895,757

[22] Filed: Jul. 17, 1997

Related U.S. Application Data

[60] Provisional application No. 60/023,289, Jul. 29, 1996.

[51] Int. Cl.⁶ ........................................................ A61B 5/00
[52] U.S. Cl. ........................... 600/549; 600/505; 600/585
[58] Field of Search ..................................... 600/554, 555, 600/585, 505, 437, 442, 459, 467; 604/95, 96, 280, 281, 282

[56] References Cited

U.S. PATENT DOCUMENTS

| | | |
|---|---|---|
| 4,776,334 | 10/1988 | Prionas . |
| 4,794,931 | 1/1989 | Yock . |
| 4,841,981 | 6/1989 | Tanabe et al. . |
| 5,000,185 | 3/1991 | Yock . |
| 5,174,299 | 12/1992 | Nelson ..................... 600/505 |
| 5,279,565 | 1/1994 | Klein et al. . |
| 5,313,949 | 5/1994 | Yock . |
| 5,336,178 | 8/1994 | Kaplan et al. . |
| 5,373,849 | 12/1994 | Maroney et al. . |
| 5,542,915 | 8/1996 | Edwards et al. . |
| 5,547,472 | 8/1996 | Onishi et al. . |
| 5,558,093 | 9/1996 | Pomeranz ................................. 600/442 |
| 5,606,974 | 3/1997 | Castellano et al. ..................... 600/462 |
| 5,682,899 | 11/1997 | Dashet et al. ........................... 600/505 |
| 5,849,028 | 12/1998 | Chen ....................................... 607/102 |

OTHER PUBLICATIONS

W Casscells et al, "Thermal detection of cellular infiltrates in living atherosclerotic plaques: possible implications for plaque rupture and thrombosis", May 25, 1996, "The Lancet".

M J Davies, "Detecting vulnerable coronary plaques", May 25, 1996, "The Lancet".

*Primary Examiner*—Cary O'Connor
*Assistant Examiner*—Pamela L. Wingood

[57] ABSTRACT

An intravascular catheter system capable of mapping thermal variations in the temperature of athrosclerotic plaque, on the athrosclerotic plaque surface, and in the arterial wall of aneurysms and other vascular lesions of the human vasculature is provided. The catheter system incorporates a plurality of thermal sensors fixedly attached along the catheters multi-lumen flexible tubular member which is adapted for insertion into the human body. Optionally, the thermal mapping catheter of the present invention is combined with other features such as intravascular ultrasound, and localized drug delivery, to provide integrated device functions.

20 Claims, 13 Drawing Sheets

CATHETER AND METHOD FOR THE THERMAL MAPPING OF HOT SPOTS IN VASCULAR LESIONS OF THE HUMAN BODY

This is a continuation in part of provisional application Ser. No. 60/023,289, filed Jul. 29, 1996, and entitled "Intravascular Catheter For Thermal Mapping of Atheroscerotic Plaque And Method Of Using Same" which is incorporated herein by reference.

BACKGROUND OF THE INVENTION

The present invention relates generally to intravascular catheter systems that utilize thermal sensors to locate and map hot spots of the atherosclerotic plaque, vascular lesions, and aneurysms in human vessels. Vulnerable plaques consist of a lipid-rich core and inflammatory cells, and these plaques are prone to rupture and erosion. Evidences indicate that plaque rupture triggers 60 to 70% of fatal myocardial infarctions. In a further 25 to 30% of fatal infarctions, plaque erosion or ulceration is the trigger. In plaque erosion, the endothelium beneath the thrombus is replaced by inflammatory cells. These inflammatory cells are associated with plaque rupture and ulceration. Both may respond to and aggravate intimal injury, promoting thrombosis and vasoconstriction.

These vulnerable plaques are often angiographically invisible. These vulnerable plaques are at a significant risk of precipitating infarction, and the majority of these plaques occur in coronary arteries that were apparently normal or only mildly stenotic on the previous angiograms. S. Ward Casscells et al have shown that plaques with a significant number of inflammatory cells and a lipid-rich core might be identifiable by the heat associated with the inflammatory process.

Intravascular ultrasonography has recently become an important diagnostic tool which allows direct visualization of plaque morphology and distribution. By way of example, Yock, U.S. Pat. No. 4,794,931, U.S. Pat. No. 5,000,185, and U.S. Pat. No. 5,313,949, and Maroney et al., U.S. Pat. No. 5,373,849 describe methods and catheters for performing intravascular ultrasonography. However, intravascular ultrasonography cannot give information on inflammatory cellular content, and is not capable of detecting temperature increase in the composition of the plaque, which is believed to be a criteria of imminent arterial thrombosis. The composition of the vulnerable plaque, particularly the presence of a large lipid core with the associated inflammatory cells, is the most powerful predictor of plaque rupture with the associated events of thrombosis and infarction.

It would be desirable then to provide a catheter which can detect and map temperature variations in the atherosclerotic plaque and on the plaque surface. These parameters can be integrated with an ultrasound catheter that can scan a plane normal to the catheters axis or distal of the catheter itself. Being able to see an increase in vulnerable plaque temperature as well as visualize the area at risk would be of great benefit to the physician, in terms of predicting potential thrombus formation/infarction and administering therapeutic intervention.

Additionally, by way of example, Klein et al., U.S. Pat. No. 5,279,565, Kaplan et al., U.S. Pat. No. 5,336,178, and Onishi et al., U.S. Pat. No. 5,547,472 describe methods and catheters for intravascular localized drug delivery. It is postulated that deliver of anti-inflammatory and antithrombotic agents directly, or adjacent to plaques at risk would reduce the likelihood of plaque rupture or ulceration and the formation of thrombus. However, at the present time these catheters are only capable of delivering the agents to angiographically identifiable plaques, and these catheters cannot distinguish vulnerable plaques from simple plaque which is not at risk of thrombosis. It would be desirable then to provide a catheter that can discriminate the stated plaque characteristics and pin point the exact delivery site, utilizing the thermal and/or ultrasonic visualization.

SUMMERY OF THE INVENTION

To achieve the foregoing and other objects and in accordance with the purpose of the present invention, an intravascular catheter is disclosed which is capable of sensing, and mapping thermal variations in the temperature of athrosclerotic plaque, on the atbrosclerotic plaque surface, and in the arterial wall of aneurysms and other vascular lesions (i.e. arteritis, vasculitis, inflammatory reaction, immunologic reaction, benign growth lesions, and malignant lesions) of the human vasculature. In various apparatus aspects of the invention, a variety of sensor arrangements and catheter construction techniques are disclosed. In some embodiments the thermal mapping is combined with other features to provide integrated device functions.

By way of example, a thermal mapping catheter, system, and method is described where a plurality of thermal sensors are fixedly attached to the outer diameter of the multilumen flexible tubular element. The spacing of the thermal sensors may be varied in accordance of the needs of a particular catheter. The thermal sensors are positioned in longitudinally rows along the distal section of the tubular element. The number of rows may vary from one to eight or more, but in a preferred embodiment four rows of sensors spaced 90 degrees apart are used. The number of thermal sensors in each row may vary from one to twenty or more, but in a preferred embodiment ten thermal sensors make up each row. It will become apparent to those skilled in the art that these thermal sensors may be infrared sensors, thermocouples, or thermisters. Unlike the thermal sensors commonly found on electrophysiology catheters which detect tissue temperatures at the time of an ablation in excess of 70 degrees centigrade, these thermal sensors sense atherosclerotic plaque temperatures between 30 degrees and 45 degrees centigrade, with the capacity to detect small temperature variations.

In another embodiment of the invention, a thermal mapping catheter apparatus, system and method is provided in which the catheter apparatus incorporating the thermal sensors is in the form of a sheath with a central lumen sized suitably for receiving an additional interventional element. By way of example, a diagnostic element such as an intravascular ultrasound catheter, or a working element such as a percutaneous transluminal coronary angioplasty catheter can be received within the central lumen of thermal mapping catheter sheath. The distal end of the thermal mapping catheter sheath is open to facilitate the advancement of a guide wire. Additionally, the central lumen of the thermal mapping catheter sheath can be sized accordingly to accept a guide wire with imaging capability as described by Pomeranz, U.S. Pat. No. 5,558,093 incorporated herein by reference.

In an additional embodiment, the distal end of the thermal mapping catheter sheath will be closed when applications do not require the use of a guide wire. It will become apparent to those skilled in the art that this thermal mapping catheter sheath can be made from an irradiated polymer that would allow itself to be thermally recovered after receiving the interventional element, fixedly attaching it to that element and creating a single multi-functional device.

And in another embodiment of the invention, a thermal mapping catheter apparatus, system and method are provided which combine the above character with an intravascular two-dimensional ultrasonography element contained in a central lumen of the thermal mapping catheters flexible tubular element. This embodiment will generate a visual and thermal image of temperature variations over the length, area, or volume of vascular lesions in the human vessel. This thermal and visual image will allow the physician to identify and evaluate the composition of the dangerous plaque, as well as to see the plaques location relative to the vessels proximal or distal segment, or its proximity to a side-branch vessel or intracoronary stent. The thermal mapping catheter apparatus can be combined with any of the currently available intravascular ultrasonography systems.

And still another embodiment of this invention provides a thermal mapping catheter apparatus, system and method which combines the above character with localized drug delivery in which the thermal mapping catheters flexible tubular element, contains a multiplicity of delivery conduits to infuse high risk areas of the vasculature with specific agents to reduce the likelihood of plaque rupture or ulceration and the formation of thrombus.

Additional objects and features of the invention will appear from the following description in which the preferred embodiments are set forth in detail in conjunction with the accompanying drawings.

BRIEF DESCRIPTION OF THE DRAWINGS

The inventions, together with further objects and advantages thereof, may best be understood by reference to the following description taken in conjunction with the accompanying drawings in which.

DETAILED DESCRIPTION OF THE DRAWINGS

Figure 1:
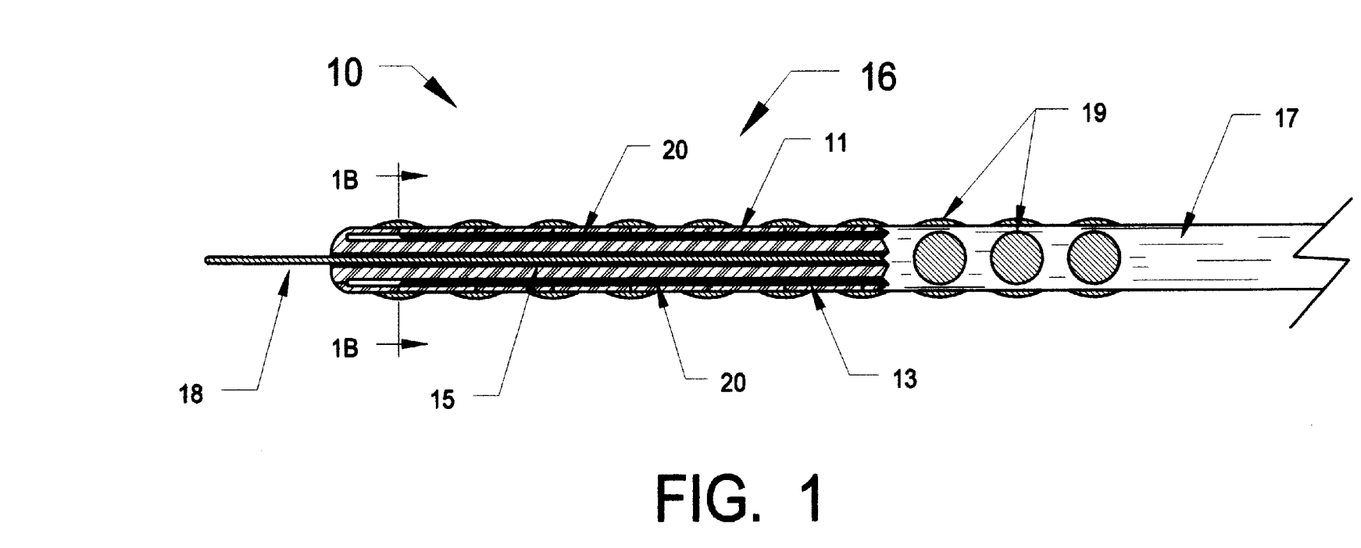
FIG. 1 is a cross sectional side view of the distal end portion of a catheter apparatus incorporating the present invention.

Several presently preferred thermal mapping catheter systems in accordance with the present invention will be described below making reference to the accompanying drawings. A first exemplary construction of a catheter apparatus 10 constructed in accordance with the principals of the present invention comprises an elongate tubular assembly 16 as seen in FIGS. 1 and 1B. The elongate tubular assembly 16 includes an elongate flexible tubular element 17 which is provided with five lumens 11, 12, 13, 14 and 15, with lumen 15 serving as a guide wire lumen. The movable guide wire 18 is shown extending through the elongate tubular assembly 16 and beyond it's distal end.

Additionally, the guide wire lumen 15 can be sized accordingly to accept a guide wire with imaging capability (not shown) as described in Pomeranz, U.S. Pat. No. 5,558,093 incorporated herein by reference. As can be seen, the flexible tubular element 17 is formed of a single extrusion with the lumens 11, 12, 13, 14, and 15, being substantially circular in cross section. It will become apparent to those skilled in the art that these lumens could be extruded in any of a variety of shapes in accordance with the needs of a particular catheter. Along the length of the elongate tubular assembly 16, are a plurality of thermal sensors 19 fixedly attached to the outside of the flexible tubular element 17. The spacing of the thermal sensors 19 may be varied in accordance with the needs of a particular catheter. However, for certain applications spacing of the thermal sensors 19 would be approximately 3 mm to 10 mm apart or more, and will be positioned in longitudinal rows along the flexible tubular element 17. The number of rows may vary from one to eight or more in accordance with the needs of a particular catheter. However, in the embodiment shown, four rows of thermal sensors 19, spaced 90 degrees apart around the axis of the flexible tubular element 17 are shown. The number of thermal sensors 19 in each row may vary from one to twenty or more in accordance with the needs of a particular catheter. However, in the embodiment shown in FIG. 1, ten thermal sensors 19 make up each row. This will allow the temperatures to be recorded along the length of a symmetrical lesion at 90 degree intervals. Additionally, the thermal sensors 19 shown in FIG. 1 and 1B and positioned 90 degrees apart along the flexible tubular element 17, make up radial bands. The number of bands formed of thermal sensors 19 may vary from one to twenty or more in accordance with the needs of a particular catheter. However, in the embodiment shown in FIG. 1, ten bands of thermal sensors 19 are shown along the length of the flexible tubular element 17. It will become apparent to those skilled in the art that the thermal sensors 19 could be any of a variety of commercially available types including, infrared, thermocouples, and thermistors. The thermal sensors 19 are attached to the flexible tubular element 17 by feeding the thermal sensor wire 20 through a pre-made pin hole at a specific point over lumen 11, 12, 13, or 14, and pulling the thermal sensor wire 20 until it extends out the proximal end of the flexible tubular element 17. The thermal sensors 19 are then held in place using a USP Class VI approved UV cured adhesive such as Dymax® 191-M, 198-M, or a cyanoacrylate adhesive such as those sold by Loctite.

Figure 1A:
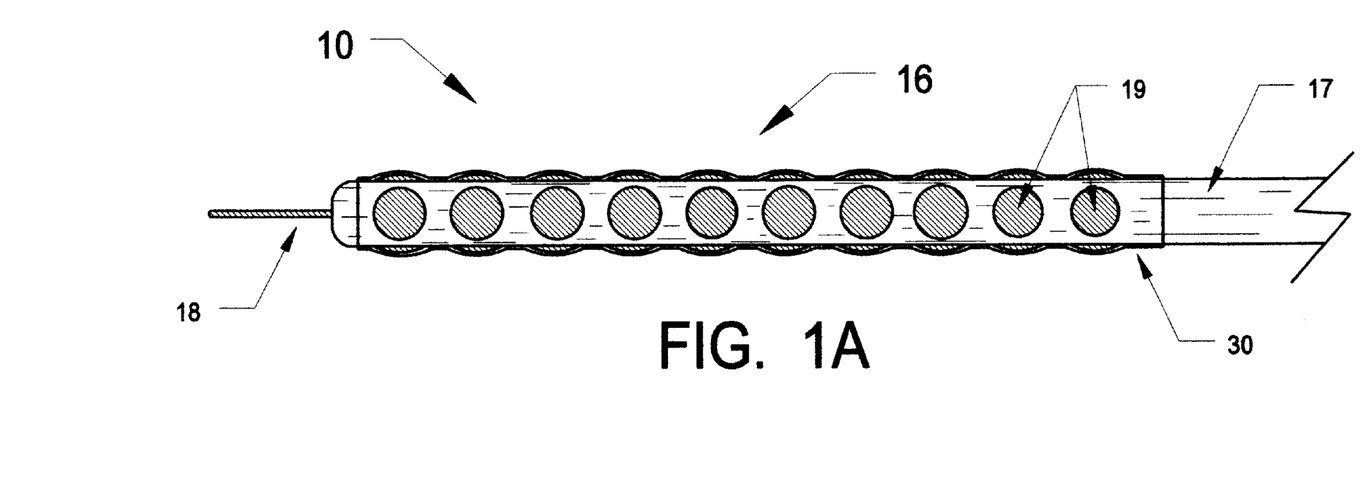
FIG. 1A is a illustrative side view of the distal portion of another embodiment of a catheter apparatus incorporating the present invention.
Figure 1B:
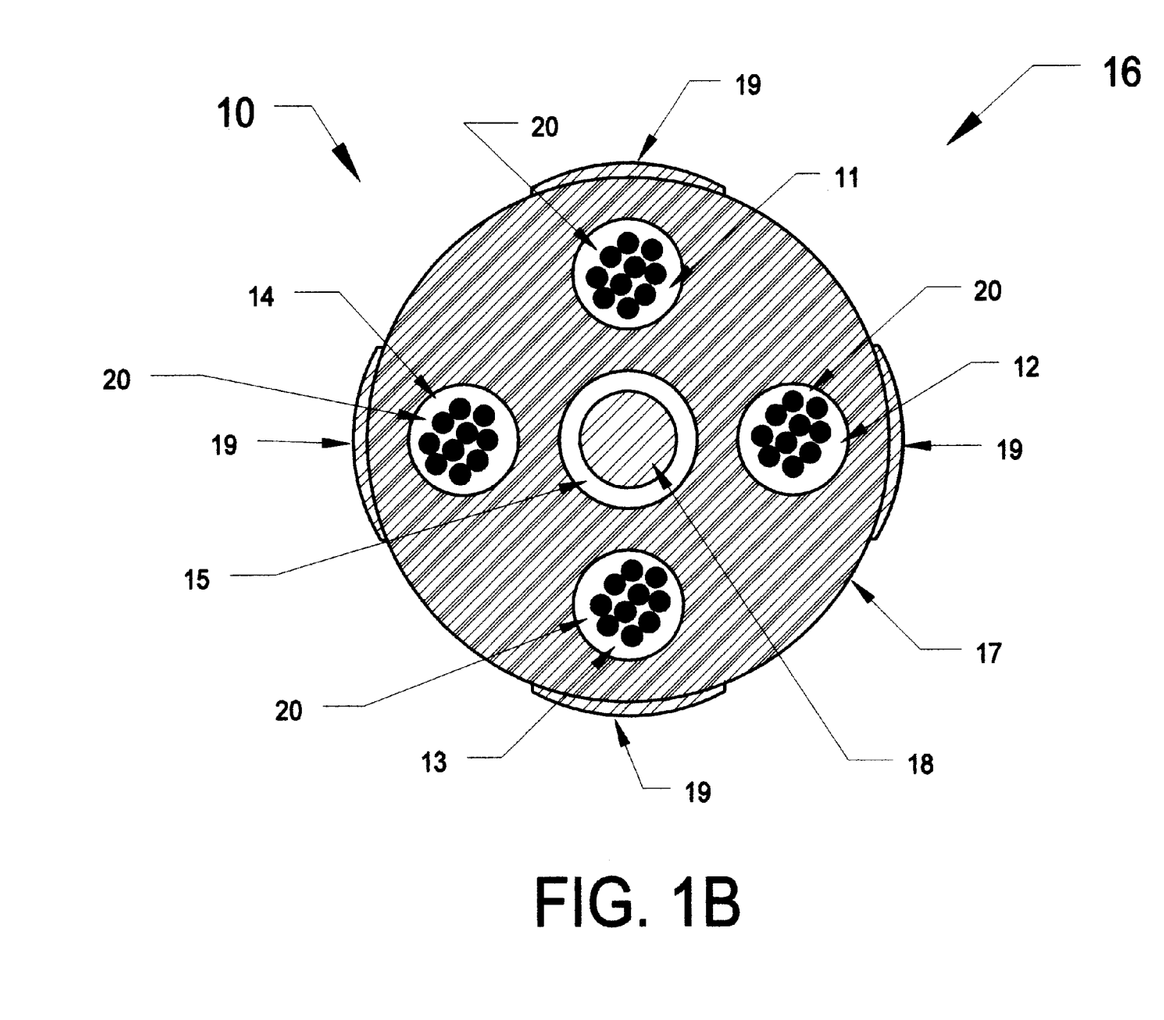
FIG. 1B is a cross sectional view taken along the lines 1B—1B of FIG. 1.

In another embodiment of the present invention shown in FIG. 1A, the thermal sensors 19 are secured in place by thermally recovering a 0.0005" to 0.002" wall, discrete band of irradiated polymer tubing 30 over the thermal sensors 19 and a portion of the flexible tubular element 17 locking them in place. Unlike the thermal sensors commonly found in close proximity to the distal tip of electrophysiology ablation catheters which detect tissue temperatures at the time of an ablation in excess of 70 degrees centigrade, these thermal sensors 19 will sense atherosclerotic plaque temperatures approximately between 30 degrees and 45 degrees centigrade, with the capacity to detect small temperature variations. The sensor wires 20 will run through the length of the flexible tubular element 17 in lumens 11, 12, 13 and 14. The thermal sensors 19 will detect the temperature and transmit the temperature measurements through the sensor wires 20, the length of the elongate tubular assembly 16 to the proximal end where the signals, are displayed on an external monitor. This signal can be displayed as numerical readings, or, the signals can be displayed as a bar graph where the increase in bar length will indicate an increase in temperature. Or, the signal can be displayed as a spike on a chart recorder where the increase in spike length will indicate an increase in temperature.

Operation of the catheter apparatus 10 shown in FIG. 1 may be described as follows. The catheter apparatus 10 is introduced into the vessel of the vasculature of the patient using normal interventional procedures and techniques. A movable guide wire 18 is used to steer the catheter to the site with the aid of angiography. The catheter is moved through the lesion until the thermal sensors 19 detected the lesions "hot spot". The area at risk is now pinpointed by it's thermal signature for a specific intervention.

Figure 2:
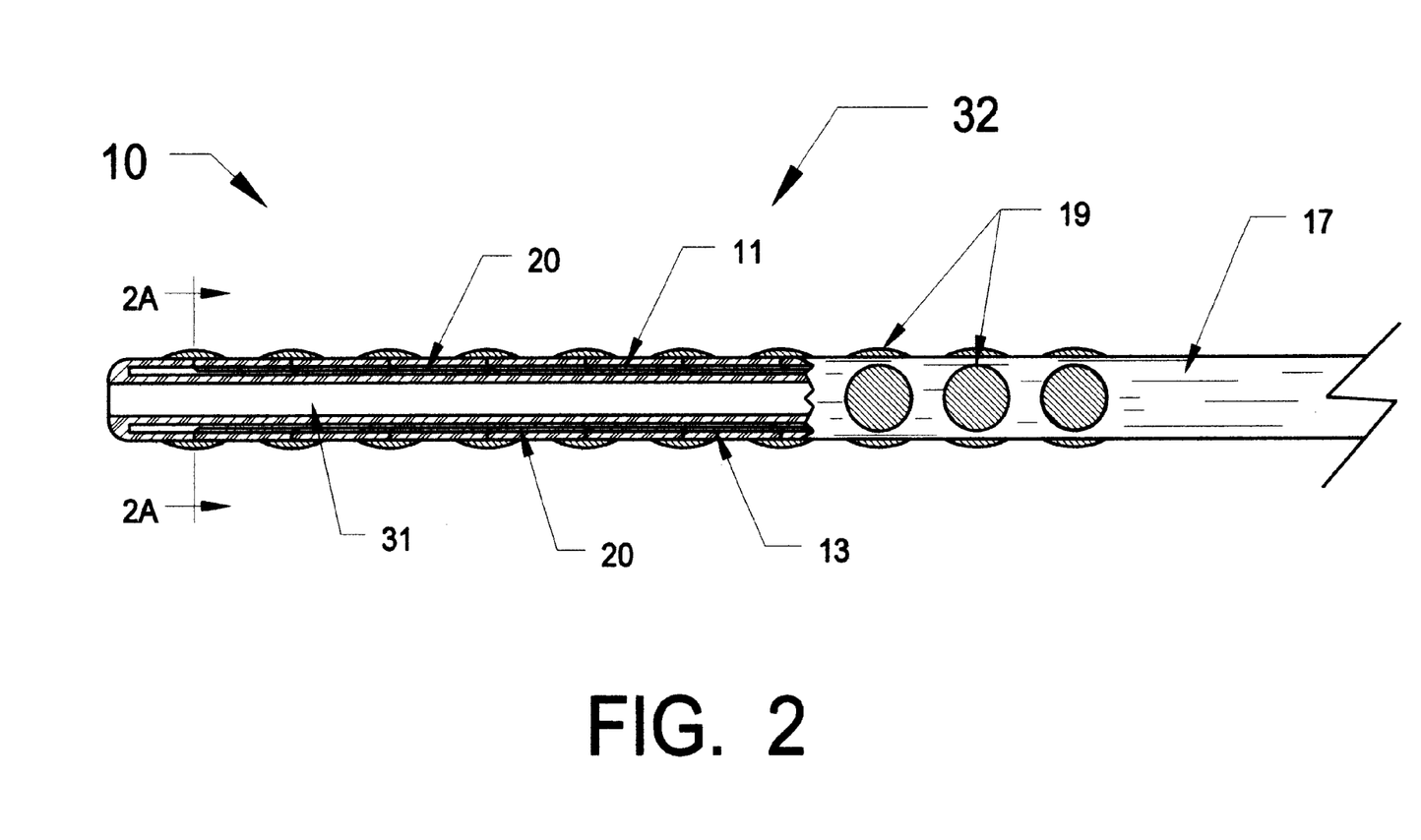
FIG. 2 is a cross sectional view of the distal portion of another embodiment of a catheter apparatus incorporating the present invention.
Figure 2A:
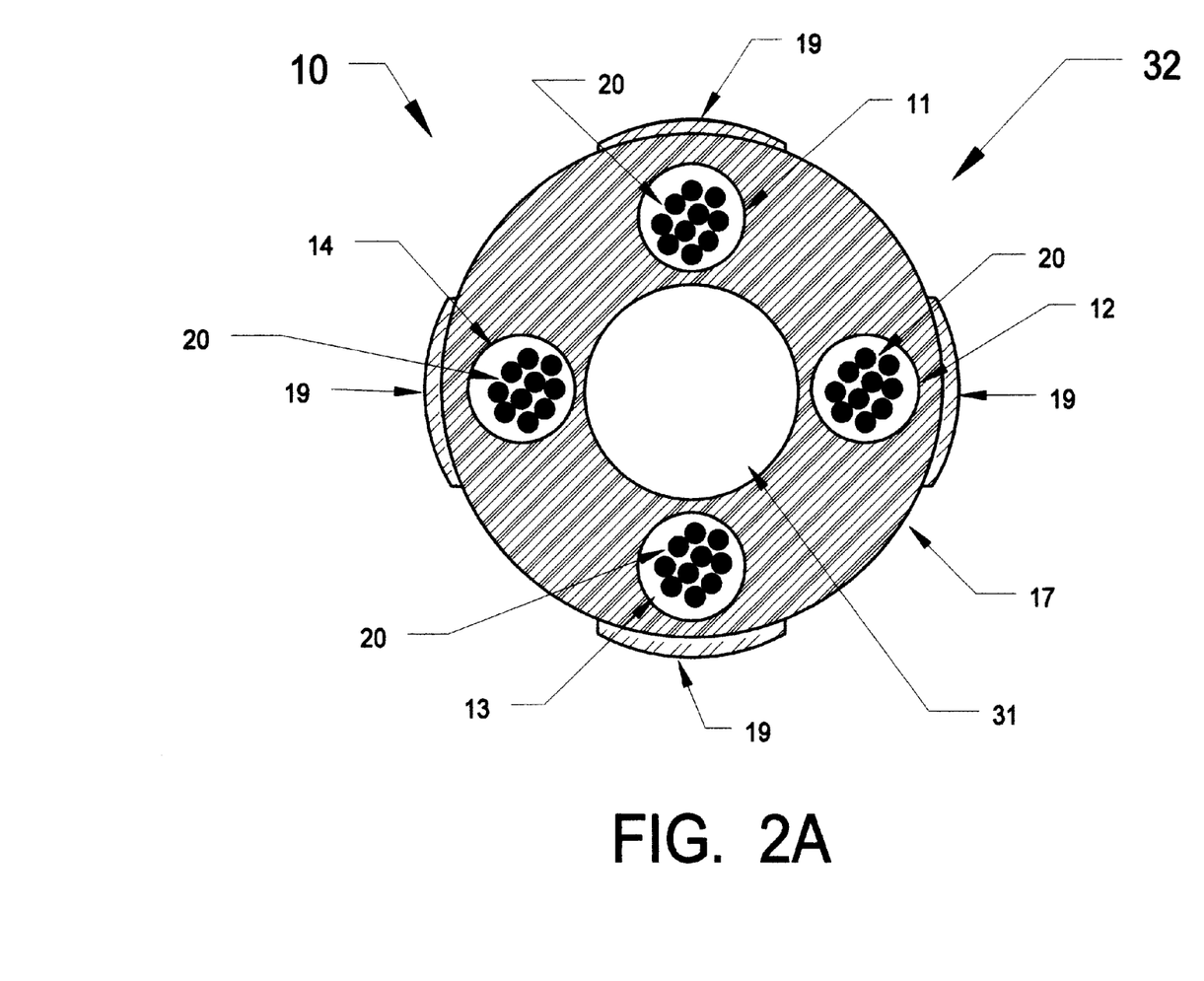
FIG. 2A is a cross sectional view taken along the lines 2A—2A of FIG. 2.

Another embodiment of the catheter apparatus 10 of the present invention is shown in FIGS. 2 and 2A, where the catheter apparatus is in the form of a sheath. The elongate tubular assembly 32 includes an elongate flexible tubular element 17 which is provided with five lumens 11, 12, 13, 14 and 31. Along the length of the elongate tubular assembly 32, are a plurality of thermal sensors 19 fixedly attached to the outside of the flexible tubular element 17. The central lumen 31 of the elongate tubular element 32 is sized suitably for receiving an intravascular catheter device therethrough. By way of example, an ultrasound catheter such as that described by Yock, U.S. Pat. No. 4,794,931, No. 5,000,185, and No. 5,313,949 or that described by Maroney et al, U.S. Pat. No. 5,373,849 which are incorporated herein by reference. It will become apparent to those skilled in the art that the elongate tubular assembly 32 can be made from an irradiated polymer that would allow itself to be thermally recovered after receiving the interventional element, fixedly attaching it to that element and creating a single multifunctional device. by The distal end of the flexible tubular element 17 is open to facilitate the advancement of a guide wire. Additionally, the distal end of the flexible tubular element 17 can be closed when applications do not require the use of a guide wire.

Figure 3:
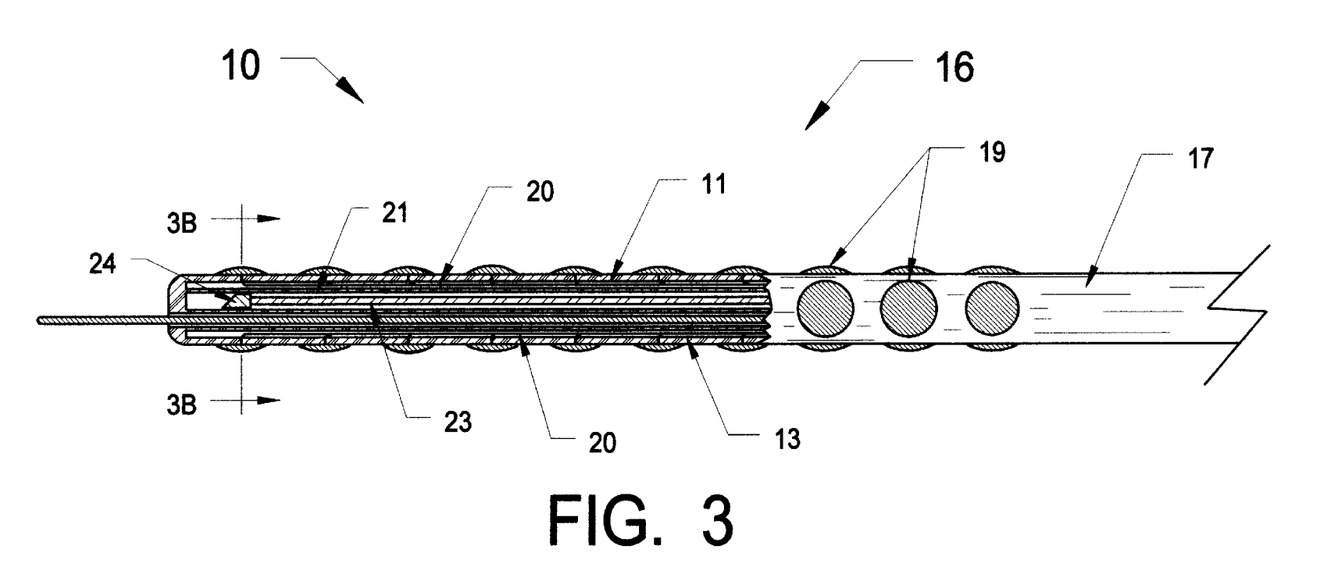
FIG. 3 is a cross sectional view of the distal portion of another embodiment of a catheter apparatus incorporating the present invention.
Figure 3A:
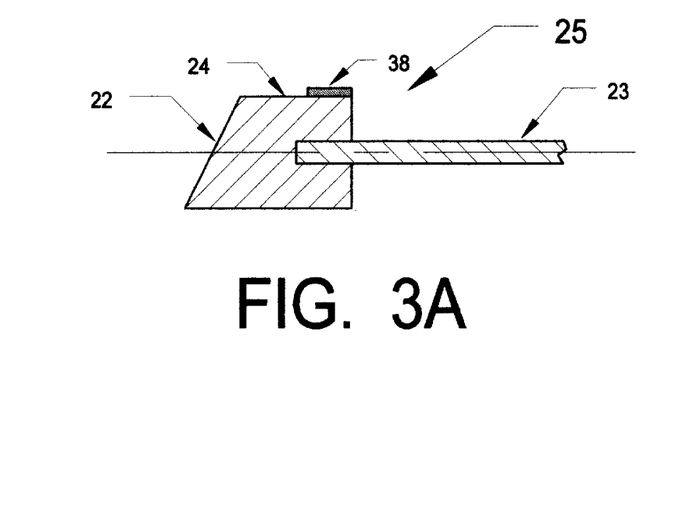
FIG. 3A is a cross sectional detail view illustrating a configuration of a reflective surface to provide a conical sweep pattern.
Figure 3B:
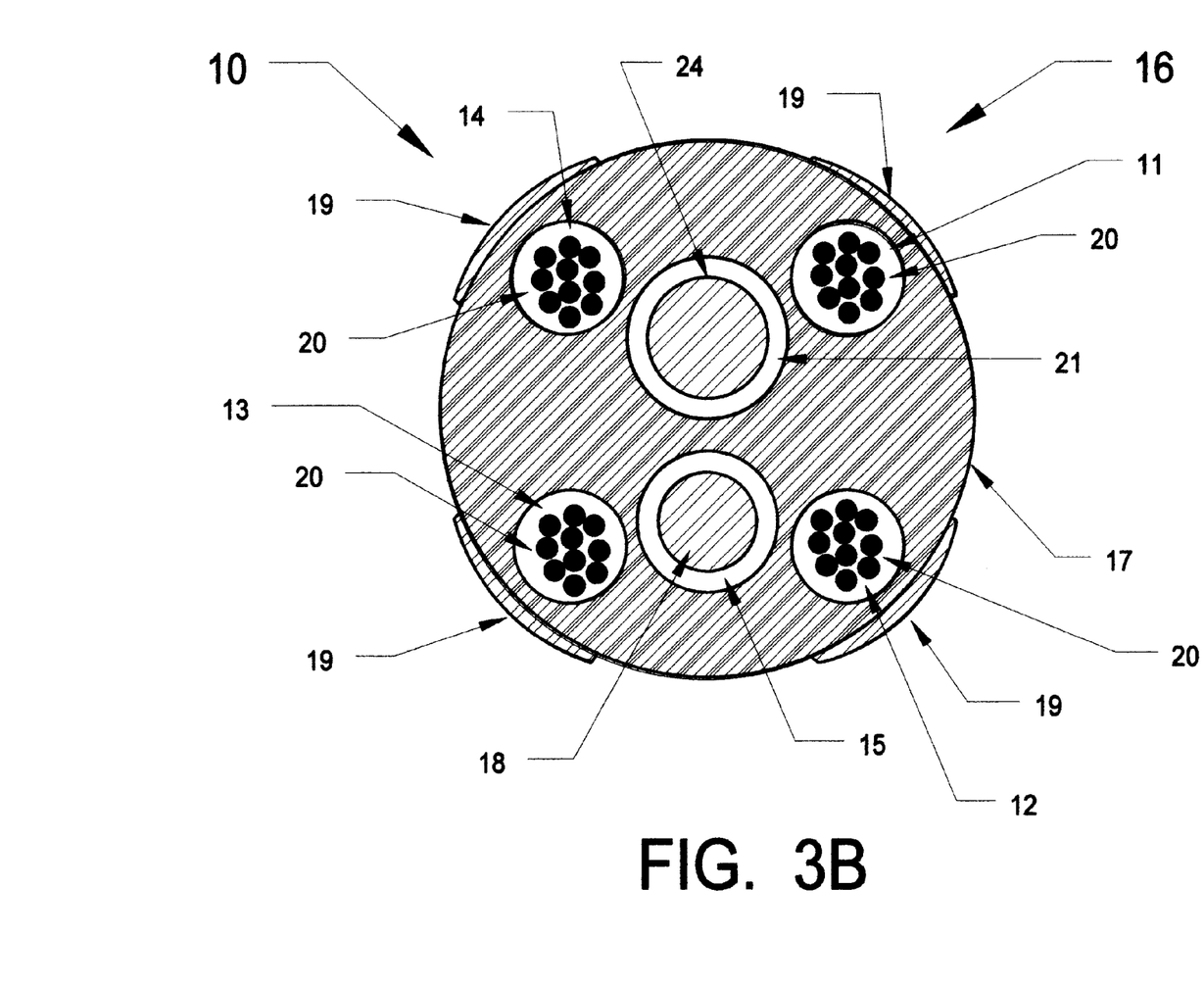
FIG. 3B is a cross sectional view taken along the lines 3B—3B of FIG. 3.

And still another embodiment of the catheter apparatus 10 of the present invention is shown in FIGS. 3, 3A, and 3B. Certain parts of this catheter apparatus 10 are very similar to those hereinbefore described and are identified by the same numbers with the exception of a two-dimensional ultrasound work element 25, typical in design, as shown in FIG. 3A. A flexible rotatable torque cable element 23 is disposed in a torque cable lumen 21 of the flexible tubular element 17. An ultrasonic transducer 24 with crystal 38 is carried by the torque cable element 23. Electrical circuitry is carried by the torque cable element 23 and is connected to the ultrasonic transducer 24 for supplying signals to and receiving signals from the reflective transducer surface 22. In the system, a transmitter is provided for supplying signals to the ultrasonic transducer 24 and a receiver is provided for receiving signals from the ultrasonic transducer 24. A motor is provided for rotating the torque cable element 23. Timing and control circuitry is provided for controlling the operation of the motor and the transmitter and receiver. A display (not shown) is provided which is operated under the control of the timing and control circuitry for displaying the image information which is received by the receiver. Along the length of the elongate tubular assembly 16 distal section, are a plurality of thermal sensors 19 fixedly attached to the outside of the flexible tubular element 17 for recording temperature signals. The sensor wires 20 would run through the length of the flexible tubular element 17 in lumens 11, 12, 13 and 14. The thermal sensors 19 would detect the temperature and transmit the temperature measurements through the sensor wires 20, the length of the flexible tubular element 17 to the proximal end where the signals, would be displayed on an external monitor. This signal can be displayed as a numerical reading. Or, the signal can be displayed as a bar graph who's increase in bar length indicates an increase in temperature. Or, the signal can be displayed as a spike on a chart recorder who's increase in spike length indicates an increase in temperature.

In a preferred embodiment, the signal would be incorporated into that of the intravascular ultrasound itself. Intravascular ultrasound or IVUS is displayed on a video screen where the different components of plaque are visualized in various shades of white, gray, and black. According to the preferred embodiment of the invention, as the ultrasound transducer 24 with thermal sensors 19 is pulled back through the plaque or inflamed lesion the thermal signal merges with the ultrasound signal causing the whites, grays, and blacks to gradually change to yellows, oranges, and reds signifying the gradual increase in plaque temperature as the transducer 24 nears and then passes through the hot spots in the plaque.

Figure 4:
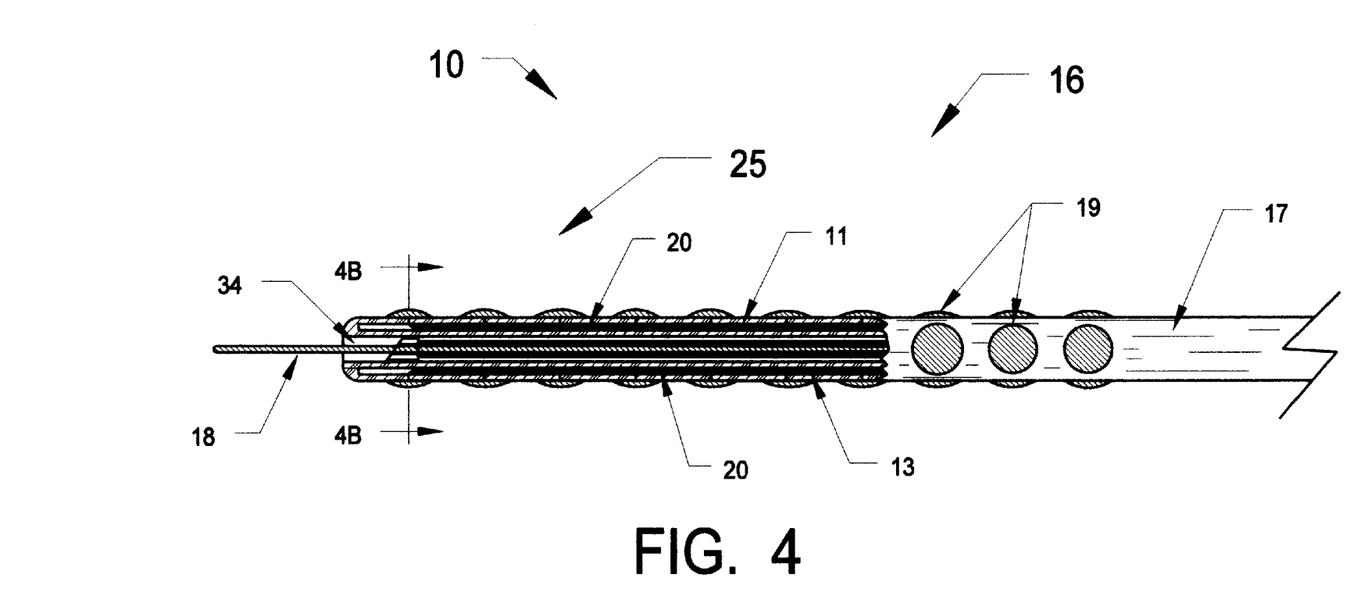
FIG. 4 is a cross sectional view of the distal portion of another embodiment of a catheter apparatus incorporating the present invention.
Figure 4A:
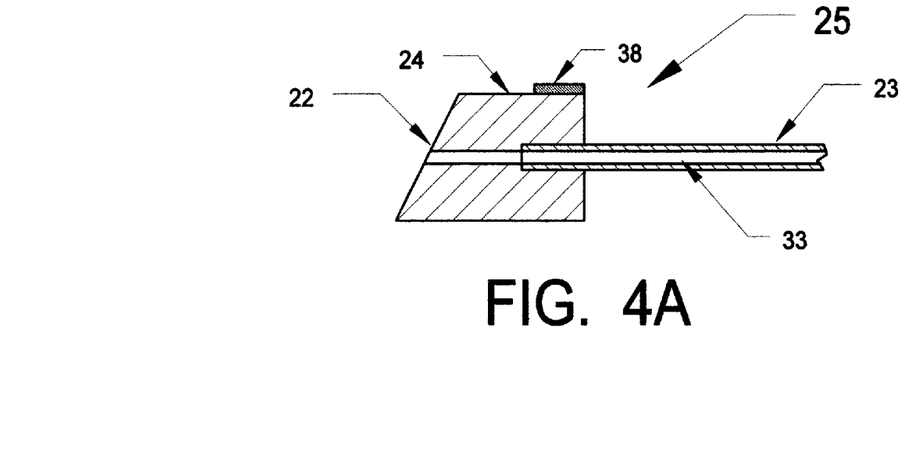
FIG. 4A is a cross sectional detail view illustrating an additional configuration of a reflective surface providing a conical sweep pattern.
Figure 4B:
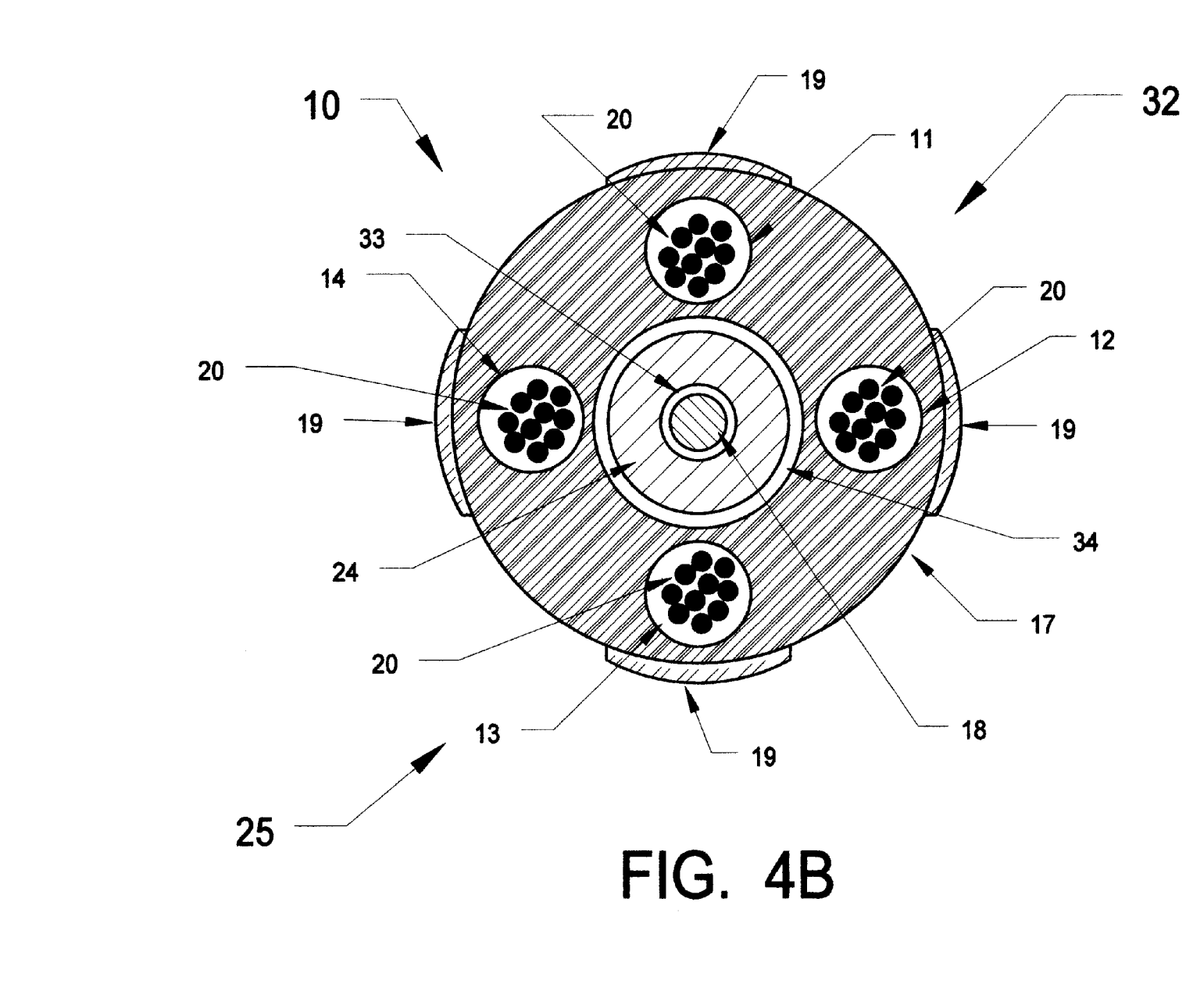
FIG. 4B is a cross sectional view taken along lines 4B—4B of FIG. 4.

And still another embodiment of the catheter apparatus 10 of the present invention is shown in FIG. 4, 4A and 4B. Certain parts of this catheter apparatus 10 are very similar to those hereinbefore described and are identified by the same numbers. In this embodiment the torque cable element 23 of the two-dimensional ultrasound work element 25 incorporates a centralized guide wire lumen 31 and is centrally located in lumen 34 of the flexible tubular element 17. The guide wire 18 would run through the length of the ultrasound work element 25 torque cable lumen 33 and out the distal end of the catheter apparatus 10.

Figure 5:
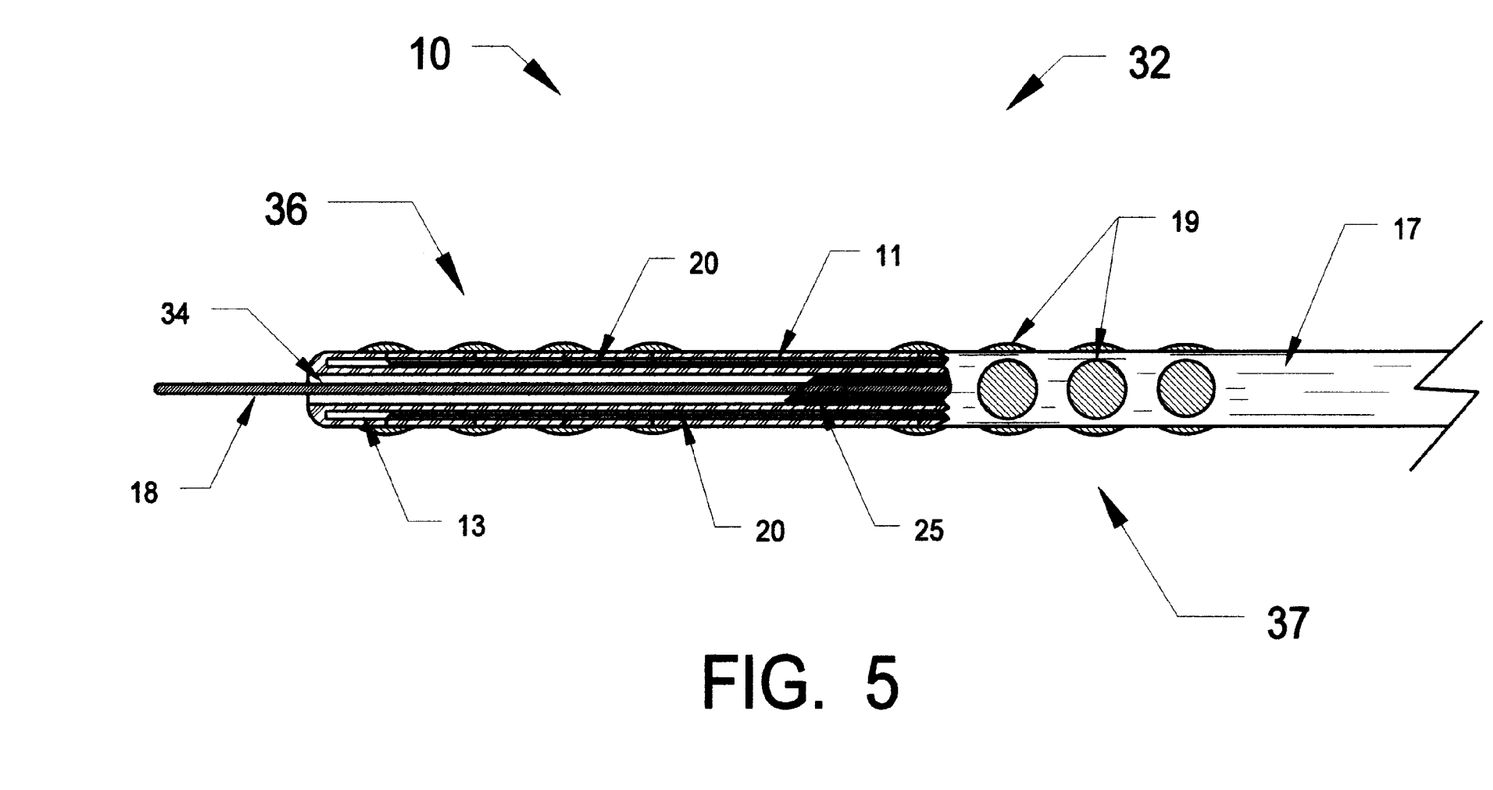
FIG. 5 is a cross sectional view of the distal portion of another embodiment of a catheter apparatus incorporating the present invention.

Another embodiment of the catheter apparatus 10 of the present invention is shown in FIG. 5. Certain parts of this catheter apparatus 10 are very similar to those hereinbefore described and are identified by the same numbers. In this embodiment the torque cable element 23 of the two-dimensional ultrasound work element 25 incorporates a centralized guide wire lumen 31 and is centrally located in lumen 34 of the flexible tubular element 17. The guide wire 18 would run through the length of the ultrasound work element 25 torque cable lumen 33 and out the distal end of the catheter apparatus 10. In this embodiment, the ultrasonic work element 25 is positioned between a distal series 36 of thermal sensors 19 and a proximal series 37 of thermal sensors 19. Both the distal series 36 and the proximal series 37 of thermal sensors 19 incorporate four rows of thermal sensors 19 spaced 3 to 10 mm apart. Each row of thermal sensors 19 is positioned 90 degrees apart around the axis of the catheter apparatus 10 flexible tubular element 17.

Figure 5A:
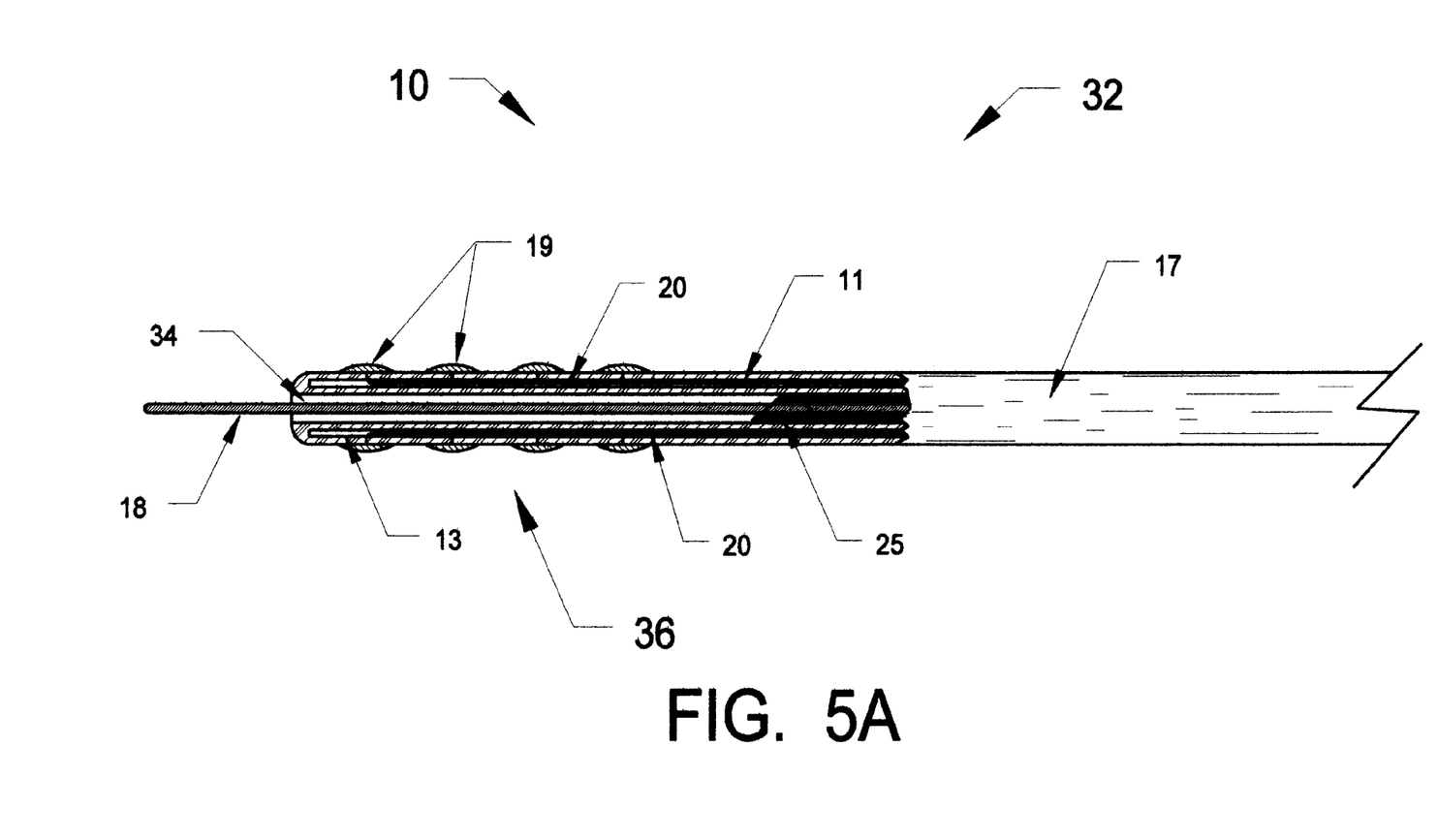
FIG. 5A is a cross sectional view of the distal portion of another embodiment of a catheter apparatus incorporating the present invention.

And still another embodiment of the catheter apparatus 10 of the present invention is shown in FIG. 5A where the ultrasonic work element 25 is positioned proximal of a distal series 36 of thermal sensors 19.

Figure 5B:
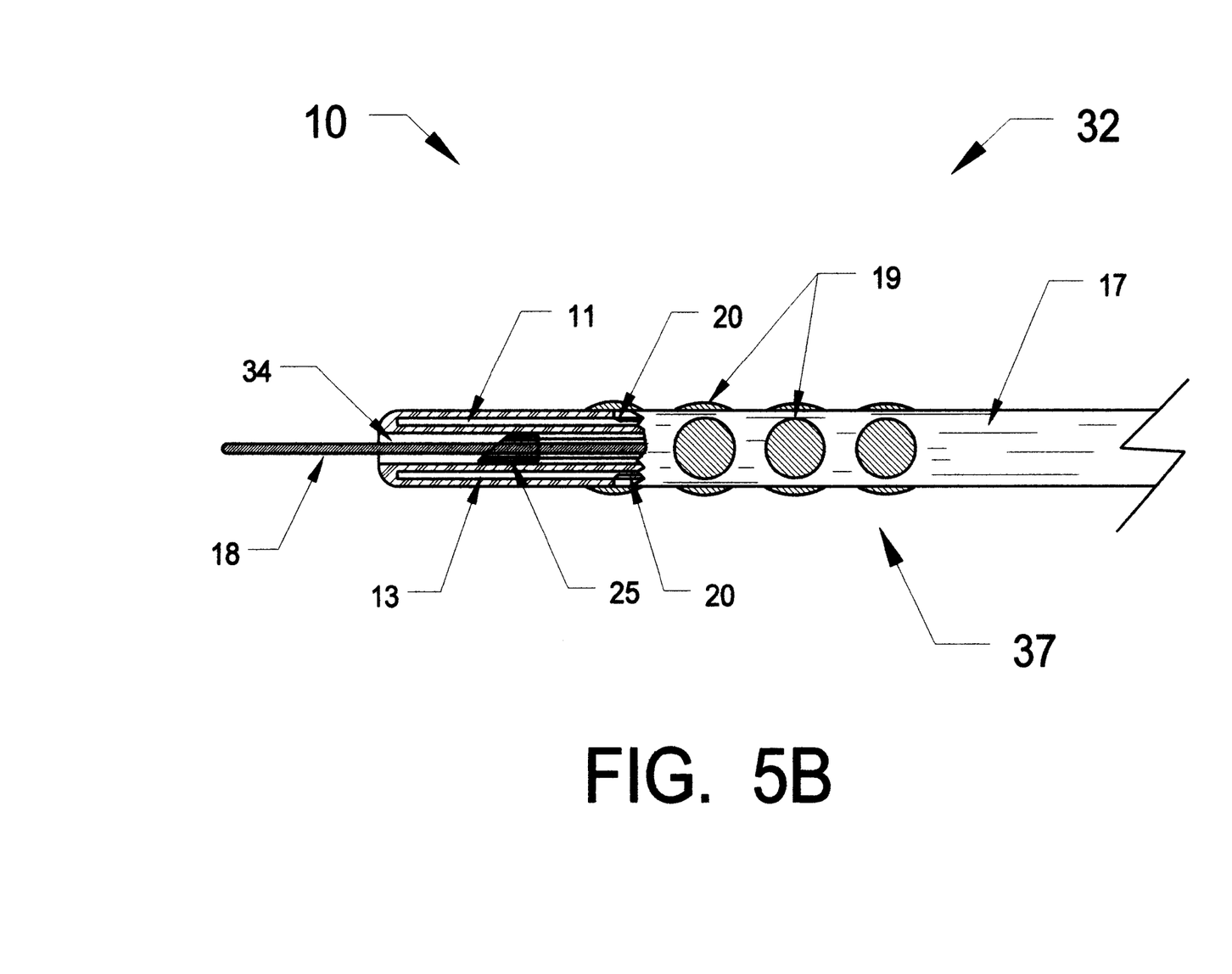
FIG. 5B is a cross sectional view of the distal portion of another embodiment of a catheter apparatus incorporating the present invention.

And still another embodiment of the catheter apparatus 10 of the present invention is shown in FIG. 5B where the ultrasonic work element 25 is positioned distal of a proximal series 37 of thermal sensors 19.

By way of example, a suitable ultrasonic work element is described in Yock, U.S. Pat. No. 4,794,931, No. 5,000,185, and No. 5,313,949 as well as Maroney et al, U.S. Pat. No. 5,373,849 which are incorporated herein by reference.

Figure 6:
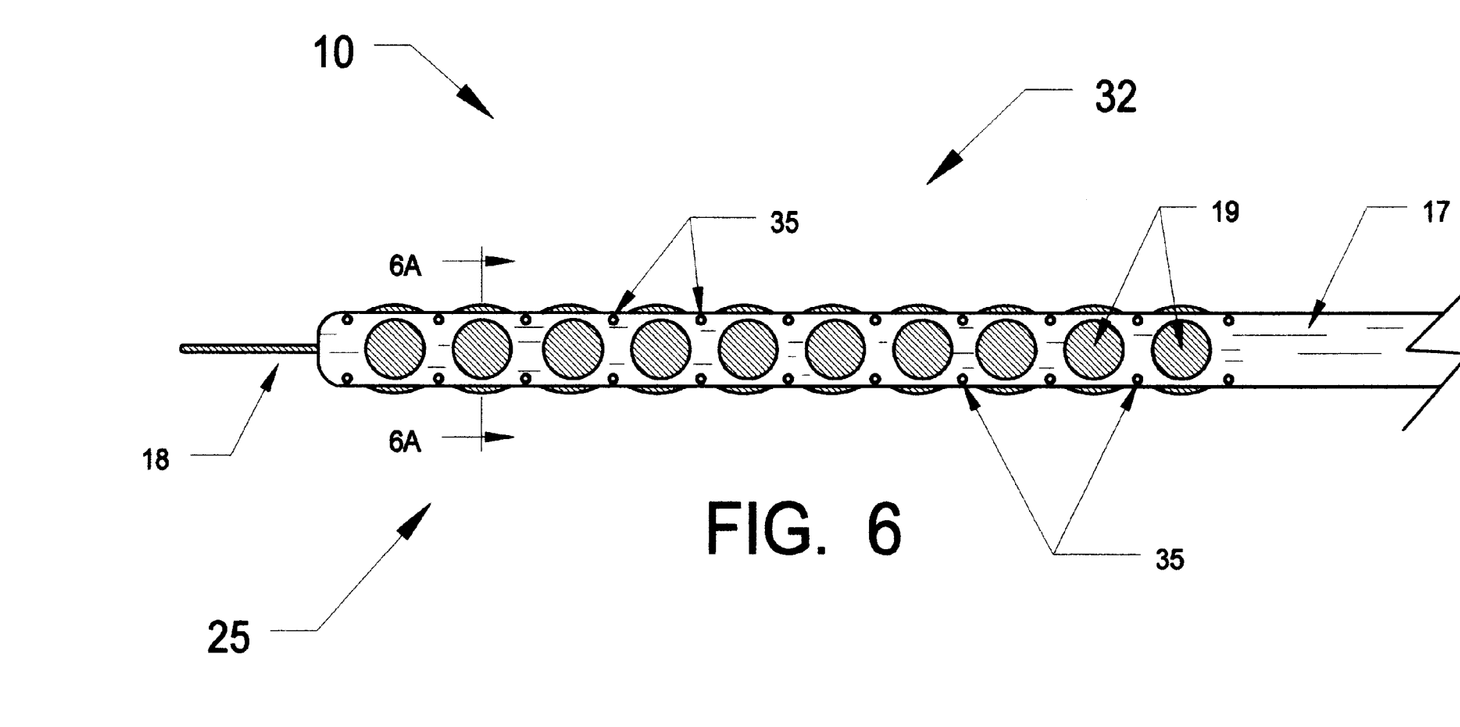
FIG. 6 is an illustrative side view of the distal portion of another embodiment of a catheter apparatus incorporating the present invention.
Figure 6A:
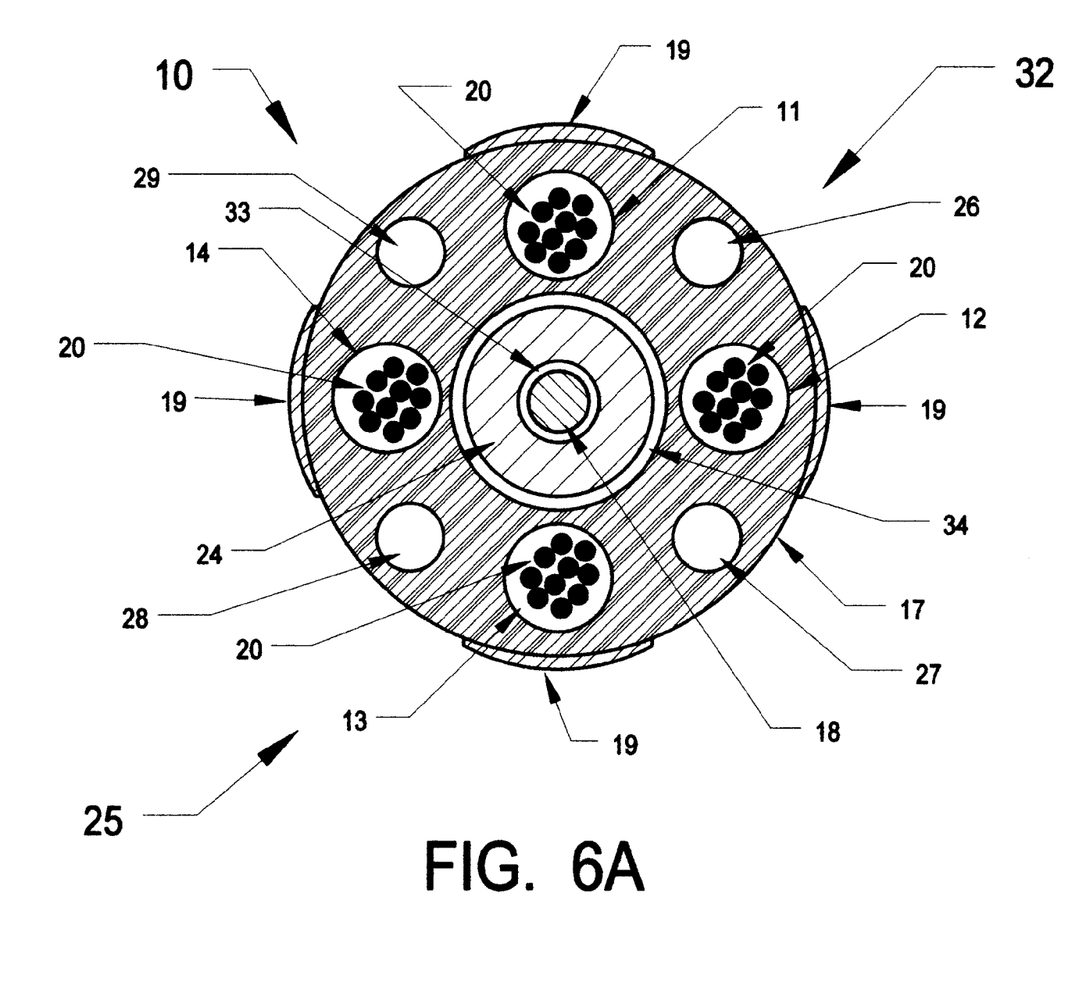
FIG. 6A is a cross sectional view taken along lines 6A—6A of FIG. 6.

In yet another embodiment of the catheter apparatus 10 of the present invention shown in FIG. 6 we see a plurality of infusion ports 35 for the purpose of delivering agents in a localized fashion to areas at risk, integrated with the ultrasonic work element 25. As seen in FIG. 6A, the catheter system comprises a series of delivery conduits 26, 27, 28, and 29 which run along the length of the flexible tubular element 17. The number of delivery conduits may vary from one to eight or more, but in a preferred embodiment, there will be four delivery conduits spaced at approximately 90 degrees about the circumference of the flexible tubular element 17 and approximately 45 degrees from the longitudinal rows of thermal sensors 19.

Other combinations are possible. For example a compliant or non-compliant balloon could be fixedly attached to the catheter apparatus 10 flexible tubular element 17 and used to place the thermal sensor 19 embodiment and or infusion port 35 embodiment in closer proximity to a high risk site in the vasculature.

Although exemplary embodiments of the present invention have been described in some detail herein, the present examples and embodiments are to be considered as illustrative and not restrictive. The invention is not to be limited to the details given, but may be modified freely within the scope of the appended claims, including equivalent constructions.

I claim:
1. A thermal mapping catheter comprising:
   an elongated flexible tubular member suitable for insertion into a vessel in the body of a patient, the flexible tubular member having a longitudinal axis and proximal and distal ends; and
   a multiplicity of thermal sensors suitable for detecting temperature variations in the body vessel, the thermal sensors being mounted on the flexible tubular member, wherein the multivucity of thermal sensors are arranged in a plurality of bands that are longitudinally spaced along the flexible tubular member, each band having a plurality of radially spaced thermal sensors.
2. A thermal mapping catheter as recited in claim 1 wherein the thermal sensors are suitable for detecting vessel temperatures in the range of approximately 30 to 45 degrees centigrade.
3. A thermal mapping catheter as recited in claim 1 wherein at least four bands are provided, and at least two thermal sensors are provided in each band.
4. A thermal mapping catheter as recited in claim 1 wherein the bands are spaced in the range of approximately 3 to 10 millimeters apart.
5. A thermal mapping catheter as recited in claim 1 further comprising a heat shrink tubing situated over at least a portion of the flexible tubular member for securing the thermal sensors to the flexible tubular member.
6. A thermal mapping catheter as recited in claim 1 wherein the flexible tubular member includes a central lumen sized suitably for receiving an interventional catheter device therethrough.
7. A thermal mapping catheter as recited in claim 1 wherein the flexible tubular member includes a central lumen sized suitably for receiving an interventional catheter device therethrough which is open at the distal end facilitating the use of a guide wire.
8. A thermal mapping catheter as recited in claim 6 wherein the interventional catheter device received into the central lumen of the flexible tubular member is a guide wire with imaging capability.
9. A thermal mapping catheter as recited in claim 1 wherein the flexible tubular member includes a central lumen sized suitably for receiving an interventional catheter device therethrough which is closed at the distal end.
10. A thermal mapping catheter as recited in claim 6 wherein the flexible tubular member is made from an irradiated material which can be thermally recovered over an interventional catheter device received in the central lumen.
11. A thermal mapping catheter as recited in claim 1 further comprising an ultrasonic imaging arrangement suitable for imaging the body vessel.
12. A thermal mapping catheter as recited in claim 11 wherein the ultrasonic imaging arrangement includes an ultrasonic transducer for emitting ultrasound signals and a torque cable for rotating the ultrasonic transducer.
13. A thermal mapping catheter comprising:
   an elongated flexible tubular member suitable for insertion into a vessel in the body of a patient, the flexible tubular member having a longitudinal axis and proximal and distal ends;
   a multiplicity of thermal sensors suitable for detecting temperature variations in the body vessel, the thermal sensors being mounted on the flexible tubular member;

an ultrasonic imaging arrangement suitable for imaging the body vessel, the ultrasonic imaging arrangement including an ultrasonic transducer for emitting ultrasound signals and a torque cable for rotating the ultrasonic transducer; and wherein the flexible tubular member includes a first lumen for receiving the torque cable and a second lumen suitable for receiving a guide wire.

14. A thermal mapping catheter as recited in claim 11 wherein; the ultrasonic imaging arrangement includes a ultrasonic transducer and a first plurality of the thermal sensors are located distally relative to the ultrasonic transducer and a second plurality of thermal sensors are located proximally relative to the ultrasonic transducer.

15. A thermal mapping catheter as recited in claim 11 wherein the ultrasonic signals received are integrated with the thermal signals received to form one signal with two distinct measurements.

16. A thermal mapping catheter as recited in claim 1 further comprising a drug delivery element suitable for delivering therapeutic agents to the body vessel.

17. A thermal mapping catheter as recited in claim 16 wherein the flexible tubular element includes a plurality of delivery conduits.

18. A thermal mapping catheter as recited in claim 16 wherein the plurality of delivery conduits has a multiplicity of infusion ports which run perpendicular to the delivery conduit along the flexible tubular member, for concentrated disbursement of infused agents.

19. A thermal mapping catheter as recited in claim 16 further comprising an ultrasonic imaging arrangement suitable for imaging the body vessel.

20. A thermal mapping catheter as recited in claim 1 wherein at least two bands are provided and at least four thermal sensors are provided in each band.

* * * * *